(12) United States Patent
Kulkarni et al.

(10) Patent No.: US 9,480,629 B2
(45) Date of Patent: Nov. 1, 2016

(54) SULFATE-FREE STRUCTURED LIQUID SURFACTANTS

(71) Applicant: RHODIA OPERATIONS, Paris (FR)

(72) Inventors: Uma A. Kulkarni, Chicago, IL (US); Frank Wagner, Frankfort, IL (US)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 14/452,738

(22) Filed: Aug. 6, 2014

(65) Prior Publication Data

US 2015/0044157 A1  Feb. 12, 2015

Related U.S. Application Data

(60) Provisional application No. 61/862,931, filed on Aug. 6, 2013.

(51) Int. Cl.
| | |
|---|---|
| *A61K 8/30* | (2006.01) |
| *A61K 8/04* | (2006.01) |
| *A61Q 19/10* | (2006.01) |
| *A61K 8/44* | (2006.01) |
| *A61K 8/55* | (2006.01) |
| *A61K 8/46* | (2006.01) |
| *A61K 8/60* | (2006.01) |
| *A61K 8/49* | (2006.01) |
| *A61Q 5/02* | (2006.01) |
| *A61Q 5/12* | (2006.01) |

(52) U.S. Cl.
CPC .......... *A61K 8/044* (2013.01); *A61K 8/44* (2013.01); *A61K 8/447* (2013.01); *A61K 8/466* (2013.01); *A61K 8/4946* (2013.01); *A61K 8/55* (2013.01); *A61K 8/602* (2013.01); *A61Q 19/10* (2013.01); *A61K 2800/10* (2013.01); *A61K 2800/596* (2013.01); *A61Q 5/02* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 8,470,753 B2 | 6/2013 | D'Aversa et al. | |
| 9,006,162 B1 * | 4/2015 | Rizk | A61K 8/42 424/70.11 |
| 2006/0019861 A1 * | 1/2006 | Potechin | A61K 8/608 510/475 |
| 2011/0280822 A1 | 11/2011 | Griffin et al. | |
| 2011/0319308 A1 | 12/2011 | Ekman Gunn et al. | |
| 2012/0021025 A1 * | 1/2012 | Bendejacq | A61K 8/0295 424/401 |

FOREIGN PATENT DOCUMENTS

| | | |
|---|---|---|
| WO | 2010012582 A2 | 2/2010 |
| WO | 2010012582 A3 | 2/2010 |

OTHER PUBLICATIONS

Gollnick, H. et al., "Topical Drug Treatment in Acne" (1998) 196(1).
"Sulfate-free made easy-Innospec launches Iselux performance blends—SOFW"; retrieved from the Internet: URL:http://www.sofw.com/index/sofw_en/sofw_en_home.html?naid=4759; (Apr. 1, 2015).
"Jane Carter Hydrating Invigorating Shampoo-CurlMart", retried from the Internet: URL: http://www.curlmart.com/product/jane-carter-hydrating-invigorating-shampoo (Apr. 1, 2015).
Mintel GNPD "Body Wash", XP-002738071 (Mar. 1, 2009).
Mintel GNPD "Shampoo", XP-002738072 (Aug. 1, 2009).

* cited by examiner

*Primary Examiner* — Robert A Wax
*Assistant Examiner* — Quanglong Truong

(57) ABSTRACT

An aqueous structured surfactant composition comprising water, one or more sulfate free anionic surfactants, one or more hydroxysultaines and one or more amphodiacetates, which is capable of suspending water insoluble or partially water soluble components. A sulfate-free structured liquid surfactant composition for use in personal care formulations allows for high level of vegetable oil and/or fragrance oil in end formula without negatively affecting stability and foam properties.

17 Claims, 2 Drawing Sheets

SULFATE-FREE STRUCTURED LIQUID SURFACTANTS

CROSS-REFERENCE TO RELATED APPLICATION

The present application claims the benefit of priority under 35 U.S.C. §119(e) of U.S. Provisional Application Ser. No. 61/862,931, filed on Aug. 6, 2013, the entire disclosure of which is incorporated herein by reference.

BACKGROUND

This invention relates to the field of sulfate-free personal care compositions such as body washes, shampoos, and hand soaps which include structured surfactants.

Structured surfactant compositions are pumpable compositions that exhibit shear-thinning viscosity and have the capacity physically to suspend water insoluble or partially water soluble ingredients. In many cases, the surfactant is present in such structured surfactant compositions in the form of packed spherulites, i.e., lamellar droplets, formed from an aqueous solution of the surfactant.

Structured surfactant compositions are useful in personal care applications, such as shampoos, body wash, hand soap, lotions, creams, conditioners, shaving products, facial washes, neutralizing shampoos, and skin treatments, in home care applications, such as liquid detergents, laundry detergents, hard surface cleansers, dish wash liquids, toilet bowl cleaners, car cleansers, and in other applications, such as oil field and agrochemical applications.

In some structured liquid compositions, relatively high levels of structurant are needed in order to create a structured system.

What is needed is a structured surfactant composition that provides typical structured surfactant properties, that is, shear-thinning viscosity and a capacity to suspend water insoluble or partially water soluble components, using a lower relative amount of structuring agent.

Conventional sulfate-free personal care compositions are comprised of water, surfactants, vegetable oils, fragrance, and other minor ingredients such as preservatives, additives, and pigments. Most such sulfate-free personal care compositions are limited to no more than 0.3% fragrance oil and/or vegetable oils which can be incorporated without affecting viscosity, foaming properties, moisturizing properties, deposition on target area. Upon increase of water insoluble compounds such as fragrance oils and vegetable oils with more than 0.5% affects stability, aesthetics and performance in terms of foam yield.

There is a strong interest in this art to provide personal care formulations which tolerate more vegetable oil. One approach to sulfate-free personal care formulations incorporates a surfactant chassis consisting of sodium lauroyl methyl isethionate, sodium lauroamphoacetate, sodium cocoyl isethionate, sodium methyl oleoyl taurate, and trisodium ethylenediamine disuccinate (Iselux SLB) available through Innospec, Inc. which is advertised as allowing up to 10% oils or other non-compatible actives.

It is an object of the present invention to address the ever increasing demand in the market for sulfate-free personal care formulations which tolerate more than 0.3 wt. % fragrance oil or vegetable oil without negatively affecting viscosity, foaming properties, moisturizing properties, deposition on target area, or stability.

SUMMARY

This object, and others which will become apparent from the following detailed description, are met by the present invention which comprises in one aspect an aqueous structured surfactant composition comprising water, one or more sulfate free anionic surfactants, and one or more amphodiacetates, said composition capable of suspending water insoluble or partially water soluble components.

In a first aspect, the present invention is directed to an aqueous structured surfactant composition, comprising water, one or more anionic surfactants, and glycinate, said composition exhibiting shear-thinning viscosity and is capable of suspending water insoluble or partially water soluble components.

In some embodiments the composition comprises a surfactant blend comprising, based on 100 parts by weight ("pbw") of the blend, from 10 pbw to 75 pbw of one or more anionic surfactants, and from greater than 1 pbw to 30 pbw of lauramidopropyl hydroxysultaine and 1 pbw to 30 pbw sodium lauroamphodiacetate.

The present invention is also directed to a method for making an aqueous structured surfactant composition, comprising mixing water, one or more anionic surfactants, and one or more amphodiacetate, wherein the composition exhibits shear-thinning viscosity and is capable of suspending water insoluble or partially water soluble components.

In another aspect the invention comprises such a composition in the form of a personal care formulation which comprises 1 to 10 wt. % vegetable and/or fragrance oil.

The personal care composition of the present invention exhibits structured surfactant properties, that is, shear-thinning viscosity and a capacity to suspend water insoluble or partially water soluble components and typically require a lower total relative amount of structuring agents.

In some embodiments the structured surfactant comprises, based on 100 parts by weight of the composition, from about 3 to about 40 parts by weight of the one or more anionic surfactants.

In certain embodiments the structured surfactant comprises from about 1 to about 70 parts by weight lauroamphodiacetate per 100 parts by weight anionic surfactant.

When used in personal care formulations certain embodiments of the sulfate-free structured liquid surfactant formulation comprise lauramidopropyl hydroxysultaine, sodium lauroamphoacetate, sodium cocoyl glycinate, sodium methyl cocoyl taurate, and decyl glucoside.

In some embodiments the composition comprises, based on 100 pbw of the composition, from greater than 0 to about 20 parts by weight of the one or more sultaines.

The composition can comprise, based on 100 pbw of the composition, from greater than 0 to about 20 parts by weight of the one or more amphoacetate and/or amphodiactetate.

The sulfate free anionic surfactants can comprise, for example, one or more compounds selected from taurates, monoalkyl phosphates, dialkyl phosphates, sarcosinates, sulfosuccinates, isethionates, and taurates and mixtures thereof.

The anionic surfactants can comprise, for example, one or more compounds selected from mild anionic amino acid based surfactants such as sodium cocoyl glycinate, sodium lauryl glycinate, sodium cocoyl alinate, glutamates, and mixtures thereof.

The surfactant chassis can be essentially "sulfate free" and "amide free."

DETAILED DESCRIPTION

Figure 1:
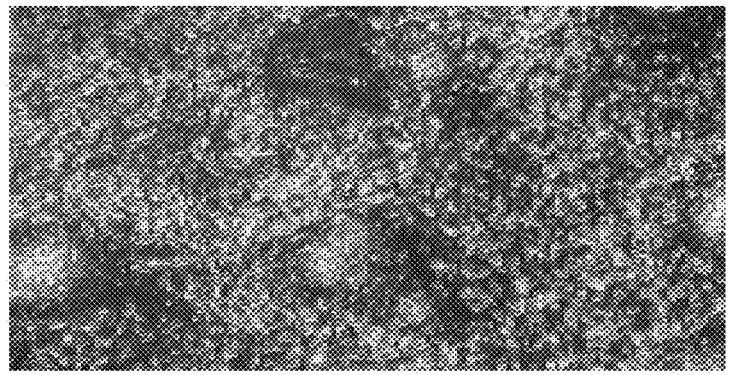
FIGS. 1-3 are arrangements observed under the microscope of the compositions of Examples 1-3, respectively.

As used herein in reference to viscosity, the terminology "shear-thinning" means that such viscosity decreases with an increase in shear rate. Shear-thinning may be characterized as a "non-Newtonian" behavior in that it differs from that of a classical Newtonian fluid, for example, water, in which viscosity is not dependent on shear rate.

As used herein in reference to a component of an aqueous composition, the terminology "water insoluble or partially water soluble components" means that the component is present in the aqueous composition at a concentration above the solubility limit of the component so that, in the case of a water insoluble component, the component remains substantially non-dissolved in the aqueous composition and, in the case of a partially water soluble component, at least a portion of such component remains un-dissolved in the aqueous composition.

As used herein, characterization of an aqueous composition as "capable of suspending", or as being "able to suspend" water insoluble or partially water insoluble components means that the composition substantially resists flotation of such components in the composition or sinking of such components in such composition so that such components appear to be neutrally buoyant in such composition and remain at least substantially suspended in such composition under the anticipated processing, storage, and use conditions for such aqueous composition.

As used herein, characterization of an aqueous composition as "capable of suspending", or as being "able to suspend" water insoluble or partially water insoluble components means that the composition substantially resists flotation of such components in the composition or sinking of such components in such composition so that such components appear to be neutrally buoyant in such composition and remain at least substantially suspended in such composition under the anticipated processing, storage, and use conditions for such aqueous composition. As used herein, the terminology "lamellar phase" means a phase that comprises a plurality of bilayers of surfactant arranged in parallel and separated by liquid medium. A lamellar phase is detectable by, for example, small angle x-ray measurement or by evidence of birefringence under a cross-polarized microscope. Lamellar phases include both spherulitic phases and the typical form of the liquid crystal G-phase, as well as mixtures thereof. "G-phases", which are sometimes referred to in the literature a $L_\alpha$ phases, are typically pumpable, non-Newtonian, anisotropic products that are cloudy looking and exhibit a characteristic "smeary" appearance on flowing. Lamellar phases, can exist in several different forms, including domains of parallel sheets which constitute the bulk of the typical G-phases described above and spherulites formed from a number of concentric spheroidal shells, each of which is a bilayer of surfactant. In this specification the term "G-phase" will be reserved for compositions which are at least partly of the former type. The spherulites are typically between 0.1 and 50 microns in diameter and so differ fundamentally from micelles. Unlike micellar solutions, spherulitic compositions are typically anisotropic and non-Newtonian. When close packed, spherulites have good solid suspending properties and are capable of suspending water insoluble or partially water soluble solids, liquids and/or gases as a separate, discontinuous phase suspended in a continuous matrix of the surfactant composition.

As used herein, the term "alkyl" means a saturated straight, branched, or cyclic hydrocarbon radical, such as for example, methyl, ethyl, n-propyl, iso-propyl, n-butyl, sec-butyl, t-butyl, pentyl, n-hexyl, cyclohexyl, decyltetradecyl, octadecyloctadecyl.

As used herein, the term "hydroxyalkyl" means an alkyl radical that is substituted with one or more hydroxyl substituents, such as for example, hydroxyethyl, hydroxypropyl.

As used herein, the term "alkoxyl" means a monovalent saturated or unsaturated straight or branched alkyl ether radical, such as for example, ethoxy, propoxy, isopropoxy, butoxy.

As used herein, the term "alkylene" means a bivalent straight or branched acyclic saturated hydrocarbon radical, including methylene and polymethylene, such as, for example, dimethylene, tetramethylene, 2-methyltrimethylene.

As used herein, the term "alkenyl" means an unsaturated straight, branched, or cyclic hydrocarbon radical having at least one carbon-carbon double bond per radical, such as for example, propenyl, butenyl.

As used herein, the term "alkyleneoxy" means a bivalent straight or branched acyclic ether or polyether radical such as, for example, ethyleneoxy, poly(ethyleneoxy), propyleneoxy, poly(propyleneoxy), poly(ethoxylenepropyleneoxy).

One embodiment of the sulfate-free structured liquid surfactant of the invention comprises lauramidopropyl hydroxysultaine, sodium lauroamphoacetate, sodium cocoyl glycinate, sodium methyl cocoyl taurate, and decyl glucoside. In one embodiment, the structured liquid surfactant concentrate chassis 'as is' comprises lauramidopropyl hydroxysultaine at about 7.5% active, sodium lauroamphoacetate at about 4.7% active, sodium cocoyl glycinate at about 6.3% active, sodium methyl cocoyl taurate at about 7.5% active, and decyl glucoside at about 5.5% active.

In one embodiment, the structured surfactant composition comprises at least one lamellar phase, said lamellar phase comprising water, at least a portion of the anionic surfactant and at least a portion of the sodium lauroamphodiacetate.

Anionic surfactants are known. Any anionic surfactant that is acceptable for use in the intended end use application is suitable as the anionic surfactant component of the composition of the present invention, including, for example, linear alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl phosphates, dialkyl phosphates, sarcosinates, sulfosuccinates, isethionates, and taurates, as well as mixtures thereof. Commonly used sulfate free anionic surfactants that are suitable as the anionic surfactant component of the composition of the present invention include, for example, sodium-monoalkyl phosphates, sodium dialkyl phosphates, sodium lauroyl sarcosinate, lauroyl sarcosine, cocoyl sarcosinate, sodium cocoyl isethionate, disodium laureth sulfosuccinate, sodium methyl oleoyl taurate, sodium methyl cocoyl taurate, sodium laureth carboxylate, sodium trideceth carboxylate, Ultra mild amino acid based anionic surfactants include, for example sodium cocoyl glycinate, sodium lauryl glycinate, Sodium Cocoyl Alinate and various glutamates and mixtures thereof.

The cation of any anionic surfactant is typically sodium but may alternatively be potassium, lithium, calcium, magnesium, ammonium, or an alkyl ammonium having up to 6 aliphatic carbon atoms including isopropylammonium, monoethanolammonium, diethanolammonium, and triethanolammonium. Ammonium and ethanolammonium salts are generally more soluble that the sodium salts. Mixtures of the above cations may be used.

In one embodiment, the structured surfactant composition of the present invention comprises, based on 100 pbw of the composition, from about 3 to about 40 pbw, more typically from about 5 to about 30 pbw, and still more typically from about 8 to about 20 pbw, of the one or more anionic surfactants.

When present in a sufficient amount relative to the amount of water and anionic surfactant components of the compositions of the present invention, the lauramphoacetate acts as a structurant for the anionic surfactant, that is, as a compound that, in combination with the water and anionic surfactant, forms a shear-thinning fluid that is capable of suspending water insoluble or partially water soluble components.

In one embodiment, the glycinate and lauroamphodiacetate is present in an amount relative to the amounts of water and anionic surfactant that is at least effective to, in combination with such water and anionic surfactant, form a shear-thinning fluid that is capable of suspending water insoluble or partially water soluble components.

In one embodiment, shear-thinning and component-suspending properties for structured surfactant compositions based on a given anionic surfactant are achieved using a amphodiacetate as a structurant, compared to the amounts of previously known structurants, such as electrolytes, fatty alcohols or alkanolamides, required to obtain such properties.

The novel sulfate-free structured surfactant of the invention is an improvement over prior sulfate-free structured surfactants in finished personal care formulations such as body washes, cleansers, and shampoos, in that it allows suspension of very high weight percentages of vegetable oil and/or fragrance oil with flash foam remaining unaffected, thereby maintaining excellent foaming properties. Another advantage is that the surfactant system permits delivery of active ingredients, fragrances, extracts, and emollients, allowing enhanced viscosity, stability, and aesthetic appearance.

The structured surfactant composition of the present invention may optionally further comprise, in addition to the anionic surfactant and amphodiacetate components of the composition of the present invention, one or more cationic surfactants, one or more additional non-ionic surfactants, one or more zwitterionic surfactants, one or more amphoteric surfactants, one or more electrolytes, or a mixture thereof. In cases where any of such optional components functions as a structurant for the anionic surfactant, each of such components may independently be present in an amount in excess of the minimum amount effective to act as a structurant. Cationic surfactants and certain non-ionic surfactants, such as such as fatty alcohols, ethoxylated alcohols, and fatty acids, are known to act as structurants for anionic surfactants.

Typically, the greater the amount of anionic surfactant present in relation to its solubility, the lesser the amount of structurant required in order to form a structure capable of supporting solid materials and/or to cause flocculation of the structured surfactant. The structurant is incorporated in an amount sufficient to promote the structured surfactant composition and may be added separately or may be included in one of the other raw materials added to the composition.

In one embodiment, the structured surfactant composition of the present invention comprises, based on 100 pbw of such composition, a total amount of up to about 40 pbw, more typically from about 0.5 to about 25 pbw and still more typically from about 1 to about 10 pbw of one or more structurants, inclusive of the amount of glycinate and lauroamphodiacetate.

Cationic surfactants are known. Any cationic surfactant that is acceptable for use in the intended end use application is suitable as the cationic surfactant component of the composition of the present invention, including, for example, cationic surfactants according to formula (IV) below:

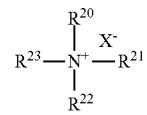

wherein: $R^{20}$, $R^{21}$, $R^{22}$, and $R^{23}$ are each independently hydrogen or an organic group, provided that at least one of $R^{20}$, $R^{21}$, $R^{22}$, and $R^{23}$ is not hydrogen, and $X^-$ is an anion.

For quaternary ammonium compounds (generally referred to as "quats") $R^{20}$, $R^{21}$, $R^{22}$, and $R^{23}$ may be the same or different organic group, but may not be hydrogen. In one embodiment, $R^{20}$, $R^{21}$, $R^{22}$, and $R^{23}$ are each ($C_8$-$C_{24}$) branched or linear hydrocarbon groups which may be substituted or interrupted by additional functional moieties and include, for example, fatty acids or derivatives thereof, including esters of fatty acids and fatty acids with alkoxylated groups, alkyl amido groups, aromatic rings, heterocyclic rings, phosphate groups, epoxy groups, and hydroxyl groups. The nitrogen atom may also be part of a heterocyclic or aromatic ring system, e.g., cetethyl morpholinium ethosulfate or steapyrium chloride. Suitable anions include, for example, chloride, bromide, methosulfate, ethosulfate, lactate, saccharinate, acetate or phosphate. Examples of quaternary ammonium compounds of the monoalkyl amine derivative type include: cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quaternium-13), stearyl dimethyl benzyl ammonium chloride (also known as stearalkonium chloride), oleyl dimethyl benzyl ammonium chloride, (also known as olealkonium chloride), lauryl/myristryl trimethyl ammonium methosulfate (also known as cocotrimonium methosulfate), cetyl-dimethyl-(2)hydroxyethyl ammonium dihydrogen phosphate (also known as hydroxyethyl cetyldimonium phosphate), bassuamidopropylkonium chloride, cocotrimonium chloride, distearyldimonium chloride, wheat germ-amidopropalkonium chloride, stearyl octyldimonium methosulfate, isostearaminopropal-konium chloride, dihydroxypropyl PEG-5 linoleaminium chloride, PEG-2 stearmonium chloride, Quaternium 18, Quaternium 80, Quaternium 82, Quaternium 84, behentrimonium chloride, dicetyl dimonium chloride, behentrimonium methosulfate, tallow trimonium chloride and behenamidopropyl ethyl dimonium ethosulfate.

Quaternary ammonium compound of the dialkyl amine derivative type distearyldimonium chloride, dicetyl dimonium chloride, stearyl octyldimonium methosulfate, dihydrogenated palmoylethyl hydroxyethylmonium methosulfate, dipalmitoylethyl hydroxyethylmonium methosulfate, dioleoylethyl hydroxyethylmonium methosulfate, hydroxypropyl bisstearyldimonium chloride, and mixtures thereof.

Quaternary ammonium compounds of the imidazoline derivative type include, for example, isostearyl benzylimidonium chloride, cocoyl benzyl hydroxyethyl imidazolinium chloride, cocoyl hydroxyethylimidazolinium PG-chloride phosphate, Quaternium 32, and stearyl hydroxyethylimidonium chloride, and mixtures thereof.

Nonionic surfactants are known. Any nonionic surfactant that is acceptable for use in the intended end use application is suitable as the optional nonionic surfactant component of the composition of the present invention, including compounds produced by the condensation of alkylene oxide groups with an organic hydrophobic compound which may be aliphatic or alkyl aromatic in nature. Examples of useful nonionic surfactants include the polyethylene, polypropylene, and polybutylene oxide condensates of alkyl phenols, fatty acid amide surfactants, polyhydroxy fatty acid amide surfactants, amine oxide surfactants, alkyl ethoxylate surfactants, alkanoyl glucose amide surfactants, and alkylpolyglycosides. Specific examples of suitable nonionic surfactants include alkanolamides such as cocamide DEA, cocamide MEA, cocamide MIPA, lauramide DEA, and lauramide MEA, alkyl amine oxides such as lauramine oxide, cocamine oxide, cocamidopropylamine oxide, and lauramidopropylamine oxide, sorbitan laurate, sorbitan distearate, fatty acids or fatty acid esters such as lauric acid, and isostearic acid, fatty alcohols or ethoxylated fatty alcohols such as lauryl alcohol, laureth-4, laureth-7, laureth-9, laureth-40, trideceth alcohol, C11-15 pareth-9, C12-13 Pareth-3, and C14-15 Pareth-11, alkylpolyglucosides such as decyl glucoside, lauryl glucoside, and coco glucoside.

Zwitterionic surfactants are known. Any Zwitterionic surfactant that is acceptable for use in the intended end use application is suitable as the optional Zwitterionic surfactant component of the composition of the present invention, including, for example, those which can be broadly described as derivatives of aliphatic quaternary ammonium, phosphonium, and sulfonium compounds in which the aliphatic radicals can be straight chain or branched and wherein one of the aliphatic substituents contains from about 8 to 18 carbon atoms and one contains an anionic water-solubilizing group such as carboxyl, sulfonate, sulfate, phosphate or phosphonate. Specific examples of suitable Zwitterionic surfactants include alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxy-propyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and alkylamidopropylhydroxy sultaines. Specific examples of suitable Zwitterionic surfactants include alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and alkylamidopropyl-hydroxy sultaines.

Amphoteric surfactants are known. Any amphoteric surfactant that is acceptable for use in the intended end use application is suitable as the optional amphoteric surfactant component of the composition of the present invention, including, for example, derivatives of aliphatic secondary and tertiary amines in which the aliphatic radical can be straight chain or branched and wherein one of the aliphatic substituents contains from about 8 to about 18 carbon atoms and one contains an anionic water solubilizing group. Specific examples of suitable amphoteric surfactants include the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl amphoglycinates, and alkyl amphopropionates, as well as alkyl iminopropionates, alkyl iminodipropionates, and alkyl amphopropylsulfonates, such as for example, cocoamphoacetate cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, and stearoamphoacetate.

In one embodiment, the structured surfactant composition of the present invention may optionally comprise, based on 100 pbw of the total amount of surfactants present in such structured surfactant composition: up to about 20 pbw, more typically from about 0.1 to about 10, and still more typically from about 0.5 to about 6, of a cationic surfactant, up to about 20 pbw, more typically from about 0.5 to 10, and still more typically from about 1 to about 6 of a nonionic surfactant, and up to about 25 pbw, more typically from about 1 to about 20, and still more typically from about 2 to about 10 of an Zwitterionic or amphoteric surfactant.

In one embodiment, the structured surfactant composition of the present invention comprises, based on 100 pbw of the composition and inclusive of any surfactant used as a structuring agent, a total amount of from about 0.1 to about 40 pbw, more typically from about 0.5 to about 30 pbw, and still more typically from about 1 to about 15 pbw, of one or more cationic surfactants, nonionic surfactants, amphoteric surfactants, and/or zwitterionic surfactants.

Electrolytes suitable as additional structurant components of the composition of the present invention include salts of multivalent anions, such as potassium pyrophosphate, potassium tripolyphosphate, and sodium or potassium citrate, salts of multivalent cations, including alkaline earth metal salts such as calcium chloride and calcium bromide, as well as zinc halides, barium chloride and calcium nitrate, salts of monovalent cations with monovalent anions, including alkali metal or ammonium halides, such as potassium chloride, sodium chloride, potassium iodide, sodium bromide, and ammonium bromide, alkali metal or ammonium nitrates, and polyelectrolytes, such as uncapped polyacrylates, polymaleates, or polycarboxylates, lignin sulphonates or naphthalene sulphonate formaldehyde copolymers. Electrolytes may be added as a separate component of the structured surfactant or may be added as a part of another component of the composition, e.g., amphoteric surfactants, such as sodium lauroamphodiacetate, lauramidopropyl hydroxysultaine and other surfactants included such as sodium cocoyl glycinate typically contain an electrolyte, such as sodium chloride.

In one embodiment, the structured surfactant composition, surfactant blend and personal care composition of the present invention each comprise from greater than 0 to about 10 pbw, more typically from about 0.5 to about 6 pbw, still more typically from about 2 to about 4 pbw of electrolyte.

The structured surfactant composition of the present invention may optionally further comprise one or more preservatives, such as benzyl alcohol, methyl paraben, propyl paraben, or imidazolidinyl urea, and DMDM hydantoin, methylisothiazolinone, methylchlorothiazolinone and may optionally further comprise one or more pH adjusting agents, such as citric acid, succinic acid, phosphoric acid, sodium hydroxide, or sodium carbonate.

The structured surfactant composition of the present invention may optionally further comprise one or more polymers and/or thickeners, chosen from the groups of clays, substituted or unsubstituted hydrocolloids, acrylates, acrylates/$C_{10-30}$ alkyl acrylates crosspolymers, such as, for example, Some examples of clays include bentonite, kaolin, montmorillonite, sodium magnesium silicate, hectorite, magnesium aluminum silicate. Some examples hydrocolloids in the unmodified form include agar, alginate, arabinoxylan, carrageenan, cellulose derivatives, such as carboxyalkyl cellulose, hydroxyalkyl cellulose, hydroxyalkyl alkyl cellulose, and alkyl cellulose, curdlan, gelatin, gellan, β-glucan, guar gum, gum arabic, locust bean gum, pectin, starch, succinoglycan, Xanthan gum. Some examples of modified or substituted hydrocolloids are cellulose derivatives, such as carboxyalkyl cellulose, hydroxyalkyl cellulose, hydroxyalkyl alkyl cellulose, alkyl cellulose, hydroxy methyl cellulose, PG-hydroxyethyl cellulose, quaternary ammonium derivatives of hydroxyethyl cellulose, quaternary ammonium derivatives of guar gum (such as Jaguar C-17, Jaguar C-14S, Jaguar Excel, Jaguar C-162 from Rhodia), hydroxypropyl guars (Jaguar HP-8, Jaguar HP-105, Jaguar HP-60, Jaguar HP-120, Jaguar C-162), modified starches, such as sodium hydroxypropyl starch phosphate (Pure-Gel 980 and Pure-Gel 998 from Grain Processing Corporation), potato starch modified (such as Structure-Solanace from National Starch), acrylate copolymers such as acrylates/aminoacrylates/C10-30 alkyl PEG-20 itaconate copolymer (such as Structure-Plus from National Starch), cationic polymers (such as Rheovis CSP, Rheovis CDE, Rheovis CDP from Ciba), polyacrylimidomethylpropane Sulfonate/Polyquaternium-4 (Plexagel ASC from ISP), hydrohobically modified nonionic polyols (Acusol 880, Acusol 882 from Rohm & Haas), and PEG-150 distearate. In general, personal care compositions may optionally comprise, based on 100 pbw of the personal care composition and independently for each such ingredient, up to about 10 pbw, typically from about 0.1 pbw to about 5.0 pbw, more typically from about 0.5 pbw to about 4.0 pbw, of such other ingredients, depending on the desired properties of the personal care composition.

In one embodiment, the structured surfactant composition is made by combining and mixing the anionic surfactant, the lauroamphodiacetate, lauramidopropyl hydroxysultaine and water and, optionally, adjusting the pH. Mixing may be applied as required to form a homogeneous solution.

Shear-thinning viscosity is measured by known viscometric methods, such as for example, using a rotational viscometer, such as a Brookfield viscometer or a cone and plate rheometer. In one embodiment, the composition of the present invention exhibits shear-thinning behavior when subjected to viscosity measurement using a Brookfield rotational viscometer, equipped with an appropriate spindle, at a rotation speed of from about 0.1 revolutions per minute ("rpm") to about 60 rpm.

The structured surfactant composition of the present invention is capable of suspending water-insoluble particles or partially water soluble components, such as vegetable oils, mineral oils, silicone oils, solid particles, abrasives, and similar articles. The composition provides a means to include otherwise difficult to incorporate components in surfactant mixtures resulting in cosmetic preparations with multi-functional benefits including, in some cases, cleansing, moisturizing, improved skin feel, exfoliation/abrasion, novel appearance, or a combination of these benefits.

The ability of a composition to suspend water insoluble or partially water insoluble components is typically evaluated by mixing the composition with sufficient vigor to entrap air bubbles in the composition and then visually observing whether the air bubbles remain entrapped in the composition for a defined period of time, such as for example, 12 to 24 hours, under defined environmental conditions, such as for example, room temperature. In one embodiment, the composition of the present invention is capable of suspending air bubbles for at least 1 week, and more typically for at least 3 months. A composition that is capable of suspending air bubbles under the for at least 12 hours at room temperature is deemed to be generally capable of suspending water insoluble or partially water soluble components in the composition under generally anticipated processing, storage, and use conditions for such composition. For components other than air, the result of the air suspension test should be confirmed by conducting an analogous suspension test using the component of interest. For unusually rigorous processing, storage and/or use conditions, more rigorous testing may be appropriate.

In one embodiment, the ability to suspend water insoluble or partially water insoluble components is evaluated under more rigorous conditions, that is, the mixed samples are visually evaluated after subjecting the samples to one or more freeze/thaw cycles, wherein each freeze/thaw cycle consists of 12 hours at $-10°$ C. and 12 hours at $25°$ C. In one embodiment, composition of the present invention remains capable of suspending air bubbles after one freeze/thaw cycle, more typically after 3 freeze/thaw cycles.

In one embodiment, the structured surfactant composition of the present invention further comprises one or more water insoluble or partially water soluble components. Such components may be in the form of a solid, a liquid, or a gas and may comprise one or more materials selected from water insoluble or partially water soluble benefit agents, such as, for example, in the case of a personal care application, emollients, conditioners, moisturizers, vitamins, vitamin derivatives, moisturizing beads, natural or synthetic abrasives, such as polyoxyethylene beads, anti-UV agents, anti-bacterial agents, anti-fungal agents, tanning accelerators, anti-aging agents, anti-wrinkle agents, antiperspirants, deodorants, essential oils, fragrances, air, or abrasives, and water insoluble or partially water soluble chemically stable appearance modifying additives such as, for example, pigments, opacifying agents, colored or reflective particles or beads such as particles of mica, titanium dioxide, or glycol stearate. It is preferred that the benefit agents are chemically stable in the chosen surfactant system.

In one embodiment, the structured surfactant composition of the present invention is present as a structured surfactant component that forms a first "phase" (which may itself comprise a plurality of phases, including aqueous phases, laminar surfactant phases and spherulitic surfactant phases, as discussed above) of a multi-phase composition that further comprises one or more additional phases that are at least substantially distinct from such first phase. As used herein in reference to the phases of a multiphase embodiments of the present invention, the terminology "substantially distinct" means that the phases each exhibit substantially homogeneous properties within a given phase and that the phases differ with respect to at least one characteristic or property, such as for example, visual characteristics, such as color, clarity, pearlescence, or physical/chemical properties, such as viscosity, lubricity, and/or benefit agent content.

In one embodiment, the structured surfactant component forms a first phase and he composition further comprises at least one additional phase that is at least substantially distinct from the first phase wherein each of such phases is a continuous phase and the phases are disposed adjacent to each other.

In one embodiment, the structured surfactant component forms a first phase and the composition further comprises at least one additional phase that is at least substantially distinct from the first phase wherein one of such phases is a continuous phase, the other of such phases is a discontinuous phase, and the discontinuous phase is dispersed within the continuous phase.

In one embodiment, the structured surfactant component forms a first phase and the composition further comprises at least one additional phase wherein that is at least substantially visually distinct from the first phase, such as for example, a composition comprising an opaque water insoluble component suspended in structured surfactant component.

In one embodiment, the structured surfactant component forms a first phase that exhibits shear-thinning viscosity and is capable of suspending water insoluble or partially water soluble components.

In one embodiment, the structured surfactant component forms a first phase, typically a continuous phase, that exhibits shear-thinning viscosity and is capable of suspending water insoluble or partially water soluble components and the composition further comprises at least one additional phase, typically a discontinuous phase, that is at least substantially distinct form the first phase, wherein the additional phase comprises one or more water insoluble or partially water soluble components.

In another embodiment, the structured surfactant component forms a first phase that exhibits shear-thinning viscosity and is capable of suspending water insoluble or partially water soluble components and the composition further comprises at least one additional phase, such as a second structured surfactant component, that is at least substantially distinct from the first phase and that exhibits shear-thinning viscosity and is capable of suspending water insoluble or partially water soluble components.

In one embodiment, the composition of the present invention comprises two distinct phases, wherein each of the phases is a continuous phase and the phases are disposed adjacent to each other.

In one embodiment, the composition of the present invention comprises two distinct phases, wherein one phase is a continuous phase, the other phase is a discontinuous phase, and the discontinuous phase is adjacent to or dispersed within the continuous phase.

In one embodiment, the composition of the present invention comprises two distinct phases, wherein each phase is a continuous phase and the two phases are disposed in a mutually interpenetrating network.

In one embodiment, a personal care composition of the present invention comprises two or more visually distinct phases. In one embodiment, the two or more visually distinct phases exhibit a visual appearance of alternating stripes.

The composition of the present invention is useful in, for example, personal care applications, such as shampoos, body wash, hand soap, lotions, creams, conditioners, shaving products, facial washes, neutralizing shampoos, personal wipes, and skin treatments, and in home care applications, such as liquid detergents, laundry detergents, hard surface cleansers, dish wash liquids, toilet bowl cleaners, as well as other applications, such as oil field and agrochemical applications.

In one embodiment, the composition of the present invention is a personal care composition.

In one embodiment, the personal care composition of the present invention comprises a structured surfactant composition of the present invention in combination with additional water and/or one or more additional ingredients and suitable personal care compositions are made by diluting the structured surfactant composition with water and/or mixing the structured surfactant composition with additional ingredients.

In one embodiment, the personal care composition consists essentially of the structured surfactant composition of the present invention, i.e., the structured surfactant composition is simply repackaged as a personal care composition.

In one embodiment, the personal care composition of the present invention further comprises one or more benefit agents, such as emollients, moisturizers, conditioners, skin conditioners, or hair conditioners such as vegetable oils, including arachis oil, castor oil, cocoa butter, coconut oil, corn oil, cotton seed oil, olive oil, palm kernel oil, rapeseed oil, safflower seed oil, sesame seed oil and soybean oil, esters, including butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, animal fats, including acetylated lanolin alcohols, lanolin, lard, mink oil and tallow, and fatty acids and alcohols, including behenic acid, palmitic acid, stearic acid, behenyl alcohol, cetyl alcohol, eicosanyl alcohol and isocetyl alcohol; vitamins or their derivatives, such as vitamin B complex, including thiamine, nicotinic acid, biotin, pantothenic acid, choline, riboflavin, vitamin B6, vitamin B12, pyridoxine, inositol, carnitine, vitamins A, C, D, E, K and their derivatives, such as vitamin A palmitate, and pro-vitamins, e.g., panthenol (pro vitamin B5), panthenol triacetate and mixtures thereof; antioxidants; free-radical scavengers; abrasives, natural or synthetic; dyes; hair coloring agents; bleaching agents; hair bleaching agents; UV absorbers, such as benzophenone, bornelone, PABA (Para Amino Benzoic Acid), butyl PABA, cinnamidopropyl trimethyl ammonium chloride, disodium distyrylbiphenyl disulfonate, potassium methoxycinnamate; anti-UV agents, such as butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, octyl dimethyl PABA (padimate O), red petrolatum; antimicrobial agents; antibacterial agents, such as bacitracin, erythromycin, triclosan, neomycin, tetracycline, chlortetracycline, benzethonium chloride, phenol, parachlorometa xylenol (PCMX), triclocarban (TCC), chlorhexidine gluconate (CHG), zinc pyrithione, selenium sulfide; antifungal agents; melanin regulators; tanning accelerators; depigmenting agents, such as retinoids such as retinol, kojic acid and its derivatives such as, for example, kojic dipalmitate, hydroquinone and its derivatives such as arbutin, transexamic acid, vitamins such as niacin, vitamin C and its derivatives, azelaic acid, placertia, licorice, extracts such as chamomile and green tea, where retinol, kojic acid, and hydroquinone are preferred; skin lightening agents such as hydroquinone, catechol and its derivatives, ascorbic acid and its derivatives; skin-coloring agents, such as dihydroxyacetone; liporegulators; weight-reduction agents; anti-acne agents; antiseborrhoeic agents; anti-ageing agents; anti-wrinkle agents; keratolytic agents; anti-inflammatory agents; anti-acne agents, such as tretinoin, isotretinoin, motretinide, adapalene, tazarotene, azelaic acid, retinol, salicylic acid, benzoyl peroxide, resorcinol, antibiotics such as tetracycline and isomers thereof, erythromycin, anti-inflammatory agents such as ibuprofen, naproxen, hetprofen, botanical extracts such as alnus, amica, artemisia capillaris, asiasarum root, calendula, chamomile. Cnidium, comfrey, fennel, galla rhois, hawthorn, houttuynia, hypericum, jujube, kiwi, licorice, magnolia, olive, peppermint, philodendron, salvia, sasa albomarginata, imidazoles such as ketoconazole and elubiol, those anti-acne agents described in Gollnick, H. et al. 196(I) Dermatology Sebaceous Glands, Acne and Related Disorders, 119-157 (1998), which is incorporated by reference herein to the extent that it is not inconsistent with the present application; refreshing agents; cicatrizing agents; vascular-protection agents; agents for the reduction of dandruff, seborrheic dermatitis, or psoriasis, such as zinc pyrithione, shale oil and derivatives thereof such as sulfonated shale oil, selenium sulfide, sulfur, salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, ciclopirox olamine, anti-psoriasis agents such as vitamin D analogs, e.g. calcipotriol, calcitriol, and tacaleitrol, vitamin A analogs such as esters of vitamin A including vitamin A palmitate, retinoids, retinols, and retinoic acid, corticosteroids such as hydrocortisone, clobetasone, butyrate, clobetasol propionate; antiperspirants or deodorants, such as aluminum chlorohydrates, aluminum zirconium chlorohydrates; immunomodulators; nourishing agents; depilating agents, such as calcium thioglycolate, magnesium thioglycolate, potassium thioglycolate, strontium thioglycolate; agents for combating hair loss; reducing agents for permanent-waving; reflectants, such as mica, alumina, calcium silicate, glycol dioleate, glycol distearate, silica, sodium magnesium fluorosilicate; essential oils and fragrances.

In one embodiment, the surfactant composition of the present invention comprises a benefit agent selected from insoluble or partially insoluble ingredients such as moisturizers or conditioners, hair coloring agents, anti-UV agents, anti-wrinkle agents, fragrances or essential oils, skin-coloring agents, anti-dandruff agents, and provides enhanced deposition of such benefit agent on the substrate, ex. Hair and/or skin or fabric or counter top or plant leaves.

In one embodiment, the personal care composition of the present invention further comprises from about 0.1 to about 50 pbw, more typically from about 0.3 to about 25 pbw, and still more typically from about 0.5 to 10 pbw, of one or more benefit agents.

The personal care composition according to the present invention may optionally further comprise other ingredients, such as, for example, preservatives such as benzyl alcohol, methyl paraben, propyl paraben and imidazolidinyl urea, thickeners and viscosity modifiers such as block polymers of ethylene oxide and propylene oxide, electrolytes, such as sodium chloride, sodium sulfate, and polyvinyl alcohol, pH adjusting agents such as citric acid, succinic acid, phosphoric acid, sodium hydroxide, and sodium carbonate, perfumes, dyes, and sequestering agents, such as disodium ethylenediamine tetra-acetate. In general, personal care compositions may optionally comprise, based on 100 pbw of the personal care composition and independently for each such ingredient, up to about 10 pbw, preferably from 0.5 pbw to about 5.0 pbw, of such other ingredients, depending on the desired properties of the personal care composition.

In general, personal care composition of the present invention may optionally comprise, based on 100 pbw of the personal care composition and independently for each such ingredient, up to about 15 pbw, preferably from 0.5 pbw to about 10 pbw, of such other ingredients, depending on the desired properties of the personal care composition.

The personal care composition of the present invention is used in a manner know in the art, for example, in the case of a cleanser or shampoo, by application of the cleanser or shampoo to the skin and/or hair and optionally rinsing the cleanser or shampoo off of the skin and/or hair with water.

In one embodiment, the structured surfactant composition, surfactant blend, and personal care composition of the present invention each comprise, based on 100 pbw of such composition. From 0 to less than 20 pbw sugar, typically from 0 to less than 10 pbw, more typically from 0 to less than 5 pbw sugar, still more typically from 0 to less than 3 pbw, and still more typically from 0 to less than 2 pbw, still more typically from 0 to less than 1 pbw, sugar per 100 pbw of the composition. In one embodiment, the structured surfactant composition, surfactant blend, and personal care composition of the present invention each comprise substantially no sugar, i.e., from 0 to less than 0.1 pbw sugar per 100 pbw of the composition, more typically no sugar, i.e., 0 pbw sugar per 100 pbw of the composition. As used herein, the term "sugar" includes monosaccharides, such as glucose and fructose, and disaccharides, such as saccharose, sucrose, lactose, and maltose, as well as mixtures thereof. Sugars are not desirable components of the structured surfactant composition or surfactant blend compositions of the present invention that are to be used in personal care applications, because sugars typically have a detrimental effect on skin feel and lubricity and may undesirably decrease foaming.

EXAMPLES

In the following examples all parts and percentages are by weight unless otherwise indicated.

Examples 1-3

A sulfate free surfactant chassis according to the invention was prepared using the ingredients listed in Table I, and let down with water. The compositions of Examples 1-3 were made by mixing the components to give the relative amounts listed in Table II. Physical properties were measured with the results set forth in Table III.

The let down step involved combining ingredients that already contained some water in relative amounts effective to provide the specified level of active ingredient.

The viscosity of each of the compositions of Examples 1-3 was measured using a Brookfield LVF Viscometer equipped with a SP #3 spindle at 12 revolutions per minute at 25° C. for 1 min for each of a series of samples that were subjected to different treatment conditions, that is, an initial viscosity measurement, after storage for 5 days at 45° C., after 5 days of 12 hour freeze (−10)/12 hour thaw (25° C.) cycling, and after 5 days storage at 4° C. The viscosity of each of the compositions of Examples 5 and 6 was measured in an analogous manner, but using a Brookfield RVF Viscometer equipped with a T bar B at 2 revolutions per minute.

The stability of each of the compositions was evaluated by visual inspection following the different treatment conditions. Results are given in the TABLES below as "stable" which indicates that the samples had remained as a single phases, and "separated", which indicates that the sample had separated into two phases when centrifuged at 20,000 G for 15 minutes in 2 milliLiter centrifuge tubes.

The ability of the compositions to suspend water insoluble or partially water insoluble components was evaluated by mixing the composition with sufficient vigor to entrap air bubbles in the composition and then visually observing whether the air bubbles remained entrapped in the composition after storing the composition overnight at room temperature.

TABLE I

| Ingredient | % wt | % Active in Concentrate |
| --- | --- | --- |
| Lauramidopropyl Hydroxysultaine | 13.51 | 6.76 |
| Sodium Lauroamphodiacetate | 16.00 | 4.96 |
| Sodium Cocoyl Glycinate | 28.00 | 6.33 |
| Sodium Methyl Cocoyl Taurate | 30.00 | 7.50 |
| Decyl Glucoside | 10.00 | 5.50 |
| Methylsiothiazolinone | 0.05 | |
| Polysorbate 20 | 0.95 | |
| Hexylene Glycol | 0.98 | |
| Phenoxyethanol | 0.51 | |

TABLE II

| Components | Example I % wt. | Example II % wt. | Example III % wt. |
| --- | --- | --- | --- |
| Water | 56.1 | 54.9 | 54.5 |
| Lauramidopropyl Hydroxysultaine | 6.6 | 5.4 | 6.1 |
| Sodium Lauroamphodiacetate | 8.0 | 6.4 | 7.2 |
| Sodium Cocoyl Glycinate | 14.0 | 11.2 | 12.6 |
| Sodium Methyl Cocoyl Taurate | 15.0 | 12.0 | 13.5 |
| Decyl Glucoside | 5.0 | 4.0 | 2.5 |
| Hydroxypropyl Guar | 0.3 | 0.3 | 0.6 |
| Guar Hydroxypropyltrimonium Chloride | 0.4 | 0.4 | 0.5 |
| Soybean Oil | 10.0 | 0.0 | 0.0 |
| Sunflower Oil | 0.0 | 0.0 | 10.0 |
| Avocado Oil | 0.0 | 10.0 | 0.0 |
| Kathon CG | 0.05 | 0.05 | 0.05 |
| Citric Acid | 0.90 | 0.9 | 0.9 |
| Fragrance: Pear Blossom | 0.30 | 1.5 | 1.5 |
| Sodium Benzoate | 0.50 | 0.5 | 0.5 |

Fragrance Pear Blossom was supplied by Mane Fragrance Company.

Physical Properties of Example 1-3—

TABLE III

| Physical Properties | Example I | | Example II | | Example III | |
| --- | --- | --- | --- | --- | --- | --- |
| | pH | Viscosity, cps LVT S# 3 @ 12 rpm | pH | Viscosity, cps LVT S# 3 @ 12 rpm | pH | Viscosity, cps LVT S# 3 @ 12 rpm |
| Initial | 5.8 | 5,369 | 5.6 | 4,500 | 5.7 | 4,000 |
| 5 days at 25° C. | 5.7 | 5,230 | 5.5 | 4,350 | 5.8 | 3,950 |
| 5 days at 45° C. | 5.6 | 5,080 | 5.6 | 3,210 | 6.0 | 2,400 |
| 5 days at 4° C. | 5.8 | 5,683 | 5.6 | 4,250 | 5.8 | 3,500 |
| 3 F/T cycles | 5.8 | 5,150 | 5.6 | 4,300 | 5.9 | 3,040 |
| Stability | 1 Month Stable | | Stable for 20 days and separated afterwards | | Stable for 15 days and separated afterwards | |
| Suspends air | Yes | | No | | No | |

5 days sample of Examples 1-3 were observed under polarize compound microscope (Model—Brunel Microscopes Ltd, United Kingdom) to observe the oil suspension in composition and notice any separation occurs. Microscopic evaluation and comparison of Example 1-3 was made along with—
 1) Control formula containing structured liquid technology that uses Miracare SLB containing Sodium Trideceth Sulfate, Sodium Lauroamphoactetate, Cocamide MEA with 10% vegetable oil and
 2) Sulfate free Body wash composition formulated with sulfate free unstructured chassis named Mackadet SFC-1 containing Disodium Lauryl Sulfosuccinate, Sodium Lauroamphohydroxypropyl Sulfonate, Cocamidopropyl Hydroxysultaine, Cocamide MIPA, Decyl Glucoside, Cocamidopropyl Betaine and with 10% Soybean Oil.

The photos in FIGS. 1-5 were taken using polarizing compound microscope camera connected to computer in the laboratory. Preliminary examination of pictures indicates fair comparison of samples for stability, separation and ability of surfactant chassis to hold high amount of water insoluble components such as vegetable oils. Close pack arrangement observed under microscope depicted strong chances of structurization in an intended test samples.

Figure 2:
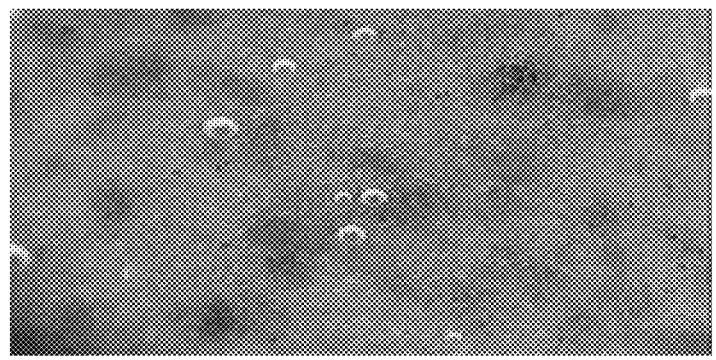
Figure 3:
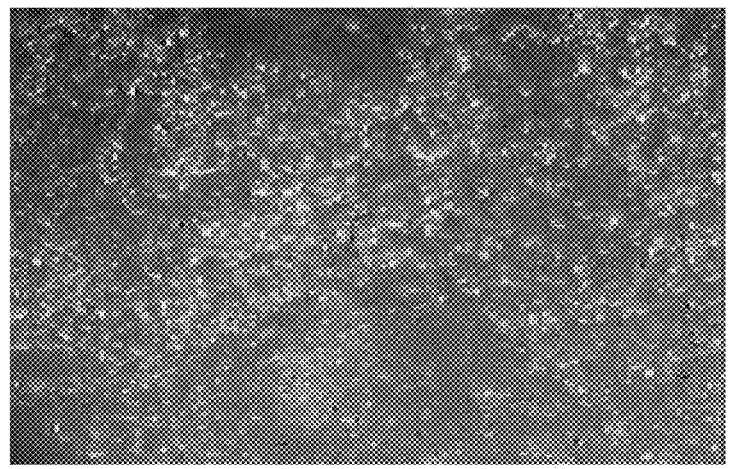

The arrangements observed under the microscope for Examples 1-3 are shown in FIGS. 1-3, respectively.

Figure 4:
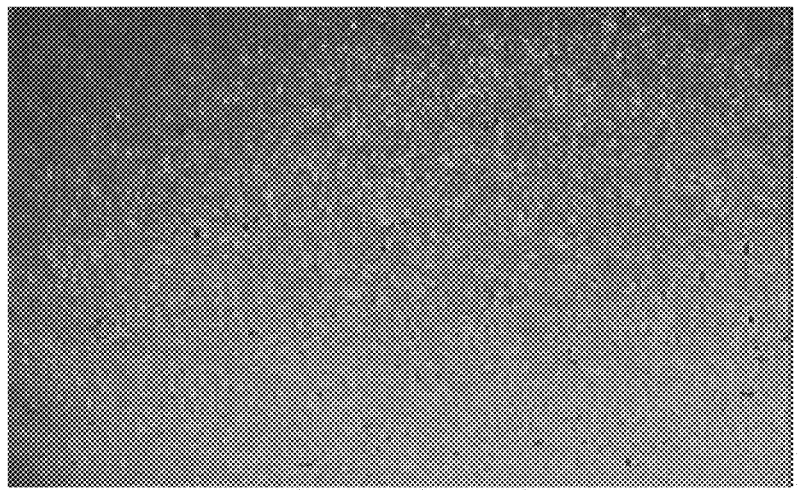
FIG. 4 is a microscopic view of a body wash formula with Miracare SLB (Structured Liquid Surfactant Chassis).

FIG. 4 illustrates a microscopic view of a body wash formula with Miracare SLB (Structured Liquid Surfactant Chassis).

Figure 5:
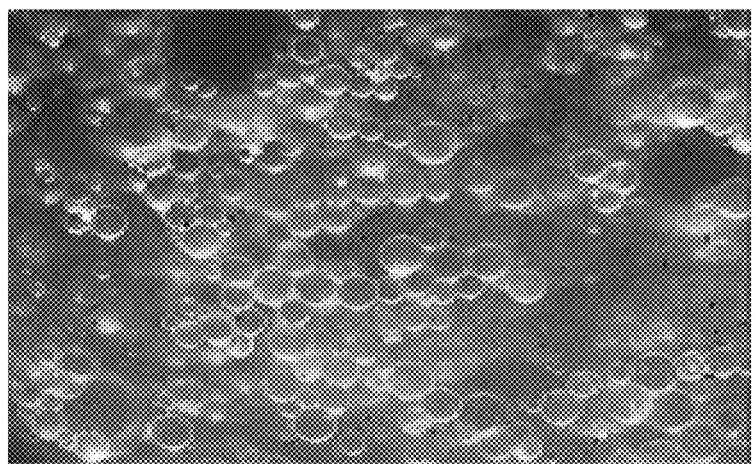
FIG. 5 is a microscopic view of a body wash formula with Mackadet SFC-1 (Sulfate Free Unstructured Surfactant Chassis).

FIG. 5 illustrates a microscopic view of a body wash formula with Mackadet SFC-1 (Sulfate Free Unstructured Surfactant Chassis).

Instant oil separation in form of big oil globules can be seen in FIG. 5 which is not evident in FIGS. 1-4. FIGS. 1-4 show close pack arrangement indicating structure formation that enables to hold high level of vegetable oils in formulation.

The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation is to be inferred. The invention is capable of considerable modification, alteration and equivalents in form and function, as will occur to those ordinarily skilled in the pertinent arts. The depicted and described preferred embodiments of the invention are exemplary only and are not exhaustive of the scope of the invention. Consequently, the invention is intended to be limited only by the spirit and scope of the appended claims, giving full cognizance to equivalents in all respects.

What is claimed is:

1. An aqueous structured surfactant composition, comprising water and lauramidopropyl hydroxysultaine at about 7.5% active, sodium lauroamphoacetate at about 4.7% active, sodium cocoyl glycinate at about 6.3% active, sodium methyl cocoyl taurate at about 7.5% active, and decyl glucoside at about 5.5% active said composition capable of suspending water insoluble or partially water soluble components.

2. The composition of claim 1, wherein the surfactant chassis is essentially sulfate free and amide free.

3. The composition of claim 1 further comprising 0.1 to 20 parts by weight of one or more water insoluble components selected from the group consisting of sunflower oil, soybean oil, avocado oil, almond oil, babassu oil, hydrogenated palm kernel oil, mink oil, olive oil, palm oil, sesame oil, soy oil, wheat germ oil.

4. A personal care composition comprising the surfactant composition according to claim 1 in the form of a body wash having 5-10 wt. % vegetable oil emollient.

5. A personal care composition comprising the surfactant composition according to claim 1 in the form of a hand soap having 3-10 wt. % vegetable oil emollient.

6. A personal care composition comprising the surfactant composition according to claim 1 in the form of a shampoo having 5-10 wt. % vegetable oil emollient.

7. A method for making an aqueous structured surfactant composition, comprising mixing water, lauramidopropyl hydroxysultaine at about 7.5% active, sodium lauroamphoacetate at about 4.7% active, sodium cocoyl glycinate at about 6.3% active, sodium methyl cocoyl taurate at about 7.5% active, and decyl glucoside at about 5.5% active wherein the composition exhibits shear-thinning viscosity and is capable of suspending water insoluble or partially water soluble components.

8. A multi-phase composition comprising: a first phase that comprises the composition of claim 1, exhibits shear-thinning viscosity, and is capable of suspending water insoluble or partially water soluble components, and one or more additional phases that are at least substantially distinct from such first phase.

9. The composition of claim 8, wherein the composition is selected from shampoos, body washes, hand soaps, lotions, creams, conditioners, shaving products, facial washes, personal wipes, and skin treatments.

10. The composition of claim 8, wherein the composition further comprises one or more benefit agents.

11. The composition of claim 8, wherein the composition structures upon addition of structurants and thickeners and upon pH adjustment towards acidic end.

12. The composition of claim 8, where in the personal care composition has pH 4.0-7.0.

13. The composition of claim 8, where in the personal care composition has "lotion like" appearance.

14. The composition of claim 8, wherein the composition further comprises, based on 100 parts by weight of such composition, from about 0.1 to about 50 parts by weight of one or more benefit agents.

15. A personal care composition comprising a sulfate-free structured liquid surfactant according to claim 1 and at least 3 wt. % vegetable oil emollient and/or fragrance oil.

16. The composition of claim 8, wherein the benefit agent comprises one or more compounds selected from emollients, moisturizers, conditioners, skin conditioners, hair conditioners, vitamins, pro-vitamins, antioxidants, free-radical scavengers, abrasives, dyes, hair coloring agents, bleaching agents, UV absorbers, anti-UV agents, antibacterial agents, antifungal agents, melanin regulators, tanning accelerators, depigmenting agents, skin lightening agents, skin-coloring agents, liporegulators, weight-reduction agents, anti-acne agents, antiseborrhoeic agents, anti-ageing agents, anti-wrinkle agents, keratolytic agents, anti-inflammatory agents, anti-acne agents, antibiotics, anti-inflammatory agents, botanical extracts, imidazoles, refreshing agents, cicatrizing agents, vascular-protection agents, agents for the reduction of dandruff, seborrheic dermatitis, or psoriasis, shale oil and derivatives thereof, anti-psoriasis agents, corticosteroids depilating agents, agents for combating hair loss, reducing agents for permanent-waving, reflectants, essential oils and fragrances.

17. An aqueous structured surfactant composition, comprising water and lauramidopropyl hydroxysultaine at about 6.8% active, sodium lauroamphoacetate at about 5% active, sodium cocoyl glycinate at about 6.3% active, sodium methyl cocoyl taurate at about 7.5% active, and decyl glucoside at about 5.5% active.

* * * * *